United States Patent [19]

Beck

[11] 4,068,660
[45] Jan. 17, 1978

[54] CATHETER PLACEMENT ASSEMBLY IMPROVEMENT

[75] Inventor: Richard William Beck, Sandy, Utah

[73] Assignee: Deseret Pharmaceutical Co., Inc., Sandy, Vt.

[21] Appl. No.: 704,716

[22] Filed: July 12, 1976

[51] Int. Cl.$^2$ .............................................. A61M 5/00
[52] U.S. Cl. ........................ 128/214.4; 128/DIG. 16; 128/348
[58] Field of Search ................... 128/214.4, 221, 348, 128/DIG. 16

[56] References Cited

U.S. PATENT DOCUMENTS

| | | | |
|---|---|---|---|
| 3,000,380 | 9/1961 | Doherty | 128/214.4 |
| 3,010,453 | 11/1961 | Doherty | 128/214.4 |
| 3,185,152 | 5/1965 | Ring | 128/214.4 |
| 3,220,411 | 11/1965 | Czorny | 128/214.4 |
| 3,703,174 | 11/1972 | Smith | 128/214.4 |
| 3,757,768 | 9/1973 | Kline | 128/348 X |

FOREIGN PATENT DOCUMENTS

| | | | |
|---|---|---|---|
| 1,064,445 | 12/1953 | France | 128/214.4 |
| 1,536,352 | 7/1968 | France | 128/214.4 |

*Primary Examiner*—Dalton L. Truluck
*Attorney, Agent, or Firm*—Lynn G. Foster

[57] ABSTRACT

A disposable assembly and associated method for placing a catheter tube or plastic cannula into the body of a patient, the assembly being initially disposed in a sterile package and comprising a straight or curved hollow cannulated needle sharpened at one end and a connector in the form of a hub at the trailing end thereof, the connector being joined to an elongated semi-rigid sheath having a longitudinal slit along one location. The flexible cannula, having a coiled wire reinforcing the trailing end thereof is initially disposed within the semi-rigid sheath with the leading end thereof resting within the hollow of the needle and the reinforced trailing end within the sheath. A stylet telescopically rests within the entire length of the plastic cannula with the exception of the leading tip thereof and is of such dimension as to stiffen the concentrically disposed plastic cannula. An inserter mechanism comprising a laterally projecting handle is connected to the trailing end of the stylet such that the handle thereof extends through the longitudinal slit in the semi-rigid sheath and is exposed for manual manipulation. The trailing end of the semi-rigid slitted sheath is plugged and/or capped to maintain sterility. In use, once the assembly has been removed from the sterile package and venipuncture has been accomplished, the catheter tube or plastic cannula is concurrently advanced into the vein with the stylet through manual manipulation of the inserter handle, so as to preserve the sterilizing of the catheter tube following which the plastic cannula is retained in the vein and, the remainder of the catheter placement assembly other than the plastic cannula is retracted rearwardly and entirely removed from the plastic cannula at the trailing end thereof and discarded. The relationship between the plastic cannula and the inserter precludes reverse displacement of the plastic cannula during insertion thereby obviating any possibility of shearing of the plastic cannula into the vein. Thereafter, a suitable plug-receiving female adapter is retrieved from the sterile package and is telescopically twisted on the exterior of the trailing end to the plastic cannula thereby deforming said trailing end between the interior helical reinforcement and the exterior adapter to accommodate fluid flow through the cannula, usually from a syringe or infusion system.

10 Claims, 7 Drawing Figures

CATHETER PLACEMENT ASSEMBLY IMPROVEMENT

BACKGROUND

1. Field of Invention

The present invention relates broadly to intravenous catheters to accommodate fluid flow into and out of the body cavities of patients and more particularly to a novel inside-the-needle apparatus for and method of placement of a soft sterile plastic cannula or catheter tube into the vein of a patient and reliable placement of a female adapter on the exposed end of the catheter prior to infusion.

2. Prior Art

Heretofore, various attempts to introduce a plastic cannula into the vein of a patient have been made. In some instances, a plastic cannula has been disposed on the outside of an insertion needle and the tube placed in the vein together. The needle is thereafter withdrawn leaving the catheter in the vein. However, the length of the plastic cannula that can be employed with this arrangement is limited to the length of the needle. In other instances, a plastic cannula has been telescopically inserted into the vein through the hollow of a needle following venipuncture. Thereafter, the needle is removed from the vein and the cannula retained therein to accommodate fluid flow. Removal of the needle "from the arm" at the trailing end of the cannula has presented certain problems. Slotted needles have sometimes been employed, the slot being wide enough so that the needle may be laterally separated from around the cannula after being withdrawn from the vein. Split needles which can be separated into two pieces and thereby removed from the cannula have also been proposed. Unslotted needles have been used and allowed to remain "on the arm" surrounding that portion of the cannula exposed outside the vein. This has created a problem of either immobilizing the patient or protecting the needle so that the patient is not injured by the needle. Typically, a needle protector has been snapped or otherwise placed about the sharpened leading tip of such a needle and the protector or cover guard thereafter secured to the arm of the patient by adhesive or the like.

Another concern which has faced the medical profession in regard to the foregoing is the maintenance of sterility of the catheter after it is removed from its package and prior to placement and use in the arm of the patient.

It has been proposed to retract and entirely remove the needle and any insertion device from the catheter tube of an inside-the-needle placement set and thereafter attach a female adapter to the trailing end of the catheter tubes to remove such from Tuohy caudal needles and thereafter placing the adapter on said catheter end.

Furthermore, other problems have been encountered in turning certain adapter-receiving reinforced ends of catheter tubes to remove such from Tuohy caudal needles and thereafter placing the adpater on said catheter end.

BRIEF SUMMARY AND OBJECTS OF THE PRESENT INVENTION

With the foregoing in mind, the present invention is intended to overcome the above mentioned obstacles and to particularly provide a unique disposable catheter placement assembly comprising an inside-the-needle catheter tube or plastic cannula wherein all parts of the assembly other than the plastic cannula are removed "off the catheter tube" and "off the arm" after venipuncture and the catheter tube is interiorly reinforced at the trailing end thereof in such a fashion to accommodate ($a$) curvilinear removal of the catheter tube from a Touhy caudal or like curved needle and ($b$) rapid and reliable placement of a female adapter at said trailing end. The venipuncture and the placement of the plastic cannula in the vein occurs procedurally in such a fashion that human hand does not contact either component and, therefore, the initial sterility of the catheter tube is maintained, independent of whether or not the user of the catheter has engaged in sterilization procedures himself. The present invention is an improvement in respect to copending U.S. patent application Ser. No. 704,715. Filed on even data herewith, the assignee of which is also the present assignee.

Accordingly, it is primary object of the present invention to provide novel methods and apparatus for placement of a plastic cannula in a body cavity of a patient.

An additional primary object of the present invention is the provision of apparatus and methods whereby the cannulated needle and insertion structure for placement of a plastic cannula through the hollow of the needle may be entirely removed from the plastic cannula and discarded following venipuncture or the like and a female adapter thereafter placed at the trailing end of the plastic cannula.

A further object of this invention is the provision for the insertion of a plastic cannula in the vein of the patient curvilinearly through the hollow of a caudal or like curved needle.

Another object of the invention is to provide a catheter tube having the trailing end flexibly stiffened to accommodate connection of the catheter tube to an intravenous infusion system.

Another object of the invention is to provide a catheter with a yieldably stiffened trailing end along with an initially separate connecting female adapter which is applied to the yieldably stiffened end of the catheter tube in sealed retained relationship to accommodate communication of fluid from an infusion system or the like.

Another object of the invention is to provide a separate female adapter for connecting to a yieldably stiffened trailing end of an indwelling pliant catheter tube wherein the material of the trailing end of the catheter tube is deformed both internally and externally to create a flexible, reliable connection.

A further object is the provision of a novel apparatus for and method of placement of a catheter tube in the vein of a patient through the hollow of a curved needle which accommodates total separation of the needle and placement apparatus from the catheter tube prior to use.

Another principal object is the provision of a catheter tube of radiopaque silicone rubber having the trailing end flexibly reinforced to accommodate curvilinear displacement and to receive a female adapter after placement in the vein of a patient.

These and other objects and features of the present invention will be apparent from the following detailed description taken with reference to the accompanying drawings.

DETAILED DESCRIPTION OF THE ILLUSTRATED EMBODIMENT

Figure 1:
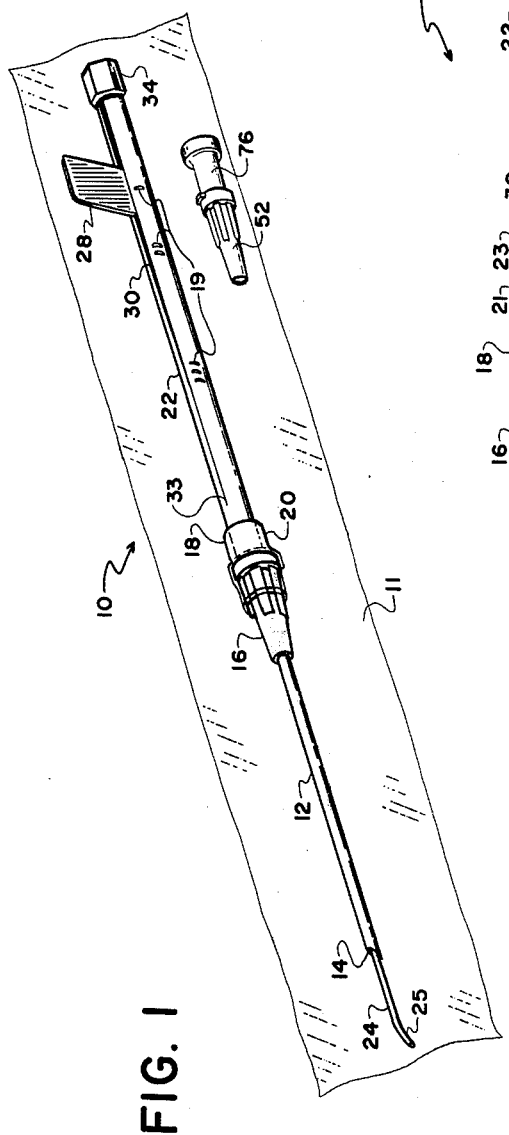
FIG. 1 is a perspective representation of a presently preferred catheter placement assembly contained within a sterile package, showing the catheter tube partially extended outisde the needle.

Reference is now made to the drawings wherein like numerals are used to designate like parts throughout and which illustrate a presently preferred sterile disposable catheter placement assembly, generally designated 10 for positioning a sterile catheter tube or plastic cannula into a body cavity of a patient, normally a vein of the cardiovascular system. FIG. 1 in particular illustrates the catheter placement assembly 10, which broadly comprises an inside-the-needle catheter placement assembly in its assembled condition, which assembly is preferably disposed in a sealed sterile package 11 following manufacture and prior to use. The package 11 also contains a female adapter 52 with a plug 76 therein for a purpose hereinafter explained.

The assembly 10 comprises a cannulated hollow metallic needle 12 which is sharpened at its leading end 14 and comprises a connector in the form of a female hub 16 at the trailing end. The hollow 17 of the connector 16 is in axial alignment with the hollow 13 of the needle 12. A sterile tubular sheath 22 of semi-rigid thin wall plastic material such as polyethylene is joined at its leading end 21 to the connector 16 by use of a sleeve 18 of heat shrinkable material. Naturally, any other mechanism other than hub 16 and sleeve 18 for connecting the trailing end of the needle to the leading end 21 of the sheath 22 so as to provide a continuous axial passageway of sufficient size would be suitable. Utilizing the sleeve 18, it is preferred that the interface between the interior of the sleeve 18 and the exterior of the leading end 21 of the sheath 22 at interface 23 receive a suitable adhesive or bonding agent to ensure proper adhesion.

The shell sheath 22 comprises a longitudinal slit 30 which commences at site 33 slightly rearward of the leading end 21 of the sheath 22 and extends along the remainder of the sheath 22. A plug 32 of suitable size is disposed within the trailing end of the tubular sheath 22 and a plastic cap 34 disposed about said trailing end. In this way the initial diameter of the tubular sheath 22 is accurately maintained so that the slit 30 is continuously urged into a closed, sterile disposition.

A catheter tube or plastic cannula 24 is initially disposed essentially entirely within the hollow of the sheath 22, the hollow 17 of the connector 16 and the hollow 13 of the needle 12, the leading end 25 of the plastic cannula 24 being initially disposed rearward of the sharpened tip 14 of the needle 12. The exact length of the catheter tube of plastic cannula 24 will naturally depend upon the combined lengths of the needle 12 and the sheath 22, each of which may be any one of several potential lengths. The outside diameter of the catheter is substantially constant and less than any and all of the inside diameters of the needle 12, the connector 16 and the sheath 22.

It is to be appreciated that the illustrated catheter tube 24 may be of radiopaque silicone rubber, sometimes referred to as silastic material, which is extremely pliable, limp and soft but highly compatible with human tissue creating little if any trauma or adverse reaction as disclosed in copending U.S. patent application Ser. No. 704,715, filed July 12, 1976 the assignee of which is also the assignee of the present application or the catheter tube may be of CLEAREX, polyvinyl chloride, (a registered trademark) TEFLON (a registered trademark) or other plastic tubular stock. It is to be emphasized that the catheter tube 24 comprises a length of hollow tubular stock unattached to any other part of the catheter placement assembly, the catheter tube being situated initially entirely within the hollow 13 of te needle, the hollow 17 of the female connector 16 and the hollow of the sheath 22.

Figure 2:
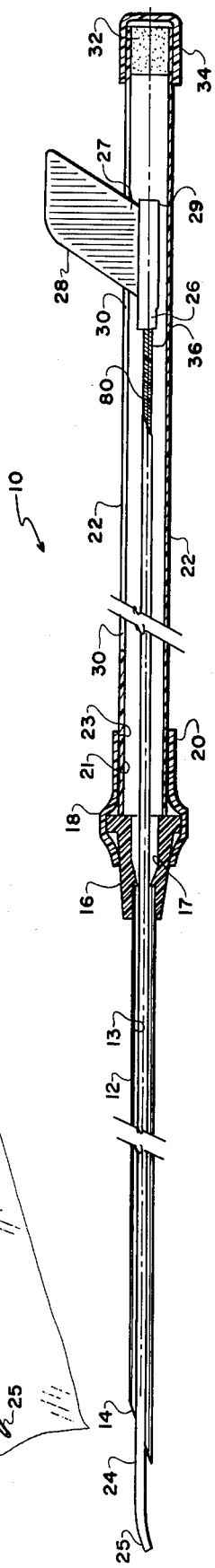
FIG. 2 is an enlarged longitudinal cross sectional representation of the catheter placement assembly of FIG. 1 again showing the catheter insertion mechanism and the catheter tube partially advanced beyond the leading end of the needle.
Figure 3:
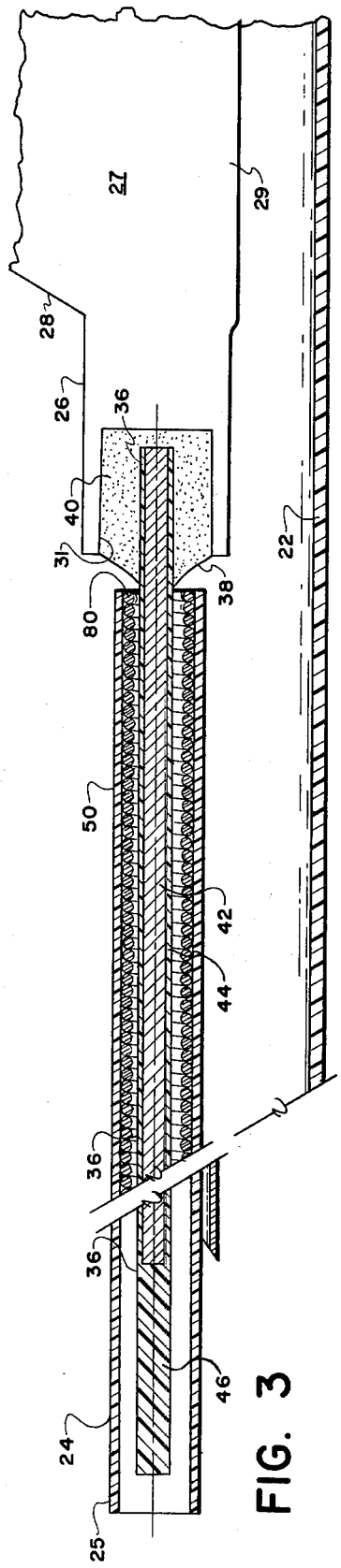
FIG. 3 is an enlarged fragmentary longitudinal cross sectional view of the trailing end of the plastic cannula or catheter tube and the insertion mechanism comprising a stiffening stylet, the trailing end of the catheter tube loosely abuts to an inserter which comprises a laterally projecting handle to manually push the catheter tube into the vein following venipuncture the trailing end of the catheter tube being interiorly flexibly reinforced by a helical wire.
Figure 5:
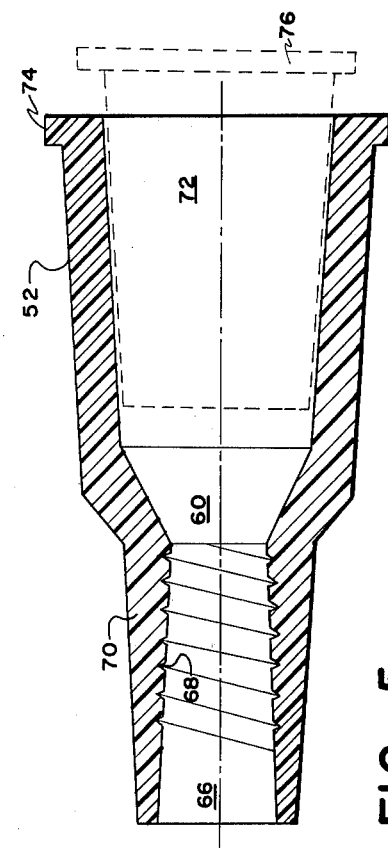
FIG. 5 is a longitudinal cross sectional view of a plug receiving fluid infusion female adapter which may be connected to the stiffened trailing end of the catheter tube.

As best seen in FIGS. 2 and 3, as part of an insertion mechanism, the stylet yieldable stiffener 36 extends through almost the entire length of the catheter tube 24, the leading end 46 of the stylet stiffener 36 terminating a short distance rearward of the distal end 25 of the catheter tube 24. While the stylet stiffener 36 may be any suitable flexible structure which will accommodate curvilinear flexing while preventing kinking, buckling, sharp bending and folding during insertion, the presently preferred and illustrated embodiment comprises a central resilient wire 42 of substantial rigidity, such as piano wire, and an exterior layer or coating of plastic 44, which prevents the wire 42 from doing any damage to the patient or the catheter tube 24. The exact outside diameter of the stiffening stylet may vary, depending upon the inside diameter of the catheter tube 24 and the amount of the stiffening desired for optimum intravenous placement of the tube 24. Not only does the stylet 36 stiffen the catheter tube, it provides an interior guide for the catheter tube during insertion. It is to be appreciated that the telescopic relation between the stiffener 36 and the catheter tube is an unattached relationship whereby the catheter tube does not follow the stiffener when the stiffener is retracted, for reasons hereinafter explained.

The trailing end 45 of the stylet 36 is anchored by epoxy or other suitable fastening material to an inserter 27. The inserter 27 is part of the overall insertion mechanism and comprises a generally cylindrical portion 29 which has a forward extension 26 and comprises an axially directed blind bore 31 into which the trailing end 45 of the stylet 36 is telescopically placed and bonded in said position by a suitable compound 40. The cylindrical inserter portion 29 is located entirely within the hollow interior of the sheath 22 rearward of the trailing end of the catheter tube 24 and loosely abuts at face 38 the trailing end of the catheter tube 24. The inserter 27 also comprises a laterally projecting handle 28 which is integral with the cylindrical portion 29 and projects from the interior of the sheath to the exterior thereof through slit 30, as best illustrated in FIG. 1.

Initially, the inserter mechanism comprising the stylet 36 and the inserter 27 with its laterally projecting handle 28 is disposed immediately adjacent the plug 32 and cap 34 closing the trailing end of the sheath 22. The insertion tab 28 is relatively thin or narrow in its width so as to minimize the amount of spreading which occurs at the slit 30. The catheter tube 24, (which is concentrically disposed about but unattached to the stylet 36), the stylet 36 and the inserter 27 may be advanced slideably in unison following venipuncture, the sheath 22 and needle 12 serving as an outside guide for such advancement and the stylet 36 comprising a stiffener and an inside guide whereby the catheter tube 24 is appropriately advanced into the vein. This advancement preserves the sterility of the catheter tube 24 within the hollow of the needle 12 and the interior of the sheath 22 and is for the most part rectilinear, although the stylet 36 and catheter tube 24 are flexed during such advancement to readily conform to the shape and orientation of the vein in which placement is occurring. The amount of flexing accommodated by the stylet 36 is restricted so that no sharp curvature may occur and, therefore, no buckling, sharp bending or kinking results in the catheter tube 24. As the inserter 27 is advanced, the slit 30 is caused to open in front of the advancing tab and close behind the tab, the user gripping the tab 28 between his fingers for such manipulation.

It should be noted that during use, the catheter tube can only be displaced in the forward direction since it is not attached to the stylet or the inserter. In other words, if the catheter tube has been partially inserted into the vein and the stylet 36 and inserter 27 are retracted, the catheter tube is not similarly retracted. Accordingly, severance (shearing) of the catheter tube 24 against the sharpened leading end 14 of the needle 12, which sometimes has been said to occur during such retraction, is entirely obviated.

The stiffener 36 also functions to assure that the passage or hollow interior of the catheter of the plastic cannula 24 is not occluded during insertion.

Marks or indicia 19 on the side of the sheath provide a visual indication of the length of the catheter tube 24 which has been displaced into the vein at any point in time.

It is to be appreciated that using tubular plastic stock having substantial rigidity and shape retaining characteristics such as certain types of polyvinyl chloride, CLEAREX (a registered trademark), and TEFLON (a registered trademark) one could eliminate much of the length of the stiffener 36 and utilize in lieu thereof a relatively short stylet which would be telescopically disposed only in the trailing end of the catheter tube 24 and thereby utilize the features of the present invention.

Venipuncture is typically accomplished by removing the assembly 10 from the package 11, gripping the assembly at connector 16 and forcing the needle tip 14 through the skin and subcutaneous tissue into the vein. Once venipuncture has occurred and the catheter tube 24 together with the stylet 36 and inserter 27 have been suitably advanced by manual manipulation of the handle 28 to place the catheter tube or plastic cannula 24 in a desired location within the vein (or other body cavity) of the patient, the entirety of the catheter placement assembly 10 (exclusive of the catheter tube 24) is removed from the catheter tube 24 and discarded. This is done by the user applying a measure of pressure to the skin over the vein and against the catheter tube 24 immediately adjacent the venipuncture site (if and to the extent necessary) and by withdrawing or retracting the needle 24 with its hub 16 together with the sheath 22, the sytlet 36 and the inserter 27. As soon as said remainder of the catheter placement assembly (excluding the catheter tube 24) has cleared the trailing end of the catheter tube, it is preferably discarded as a unit, although separate removal of (a) the stylet and inserter, (b) the sheath (if the bond at sleeve 18 permits), and (c) the needle 12 and connector 18 could be resorted to.

At this point in time, it is requisite that the catheter tube 24, with the forward portion in the vein, be suitably equipped to accommodate fluid flow. For example, if fluid infusion into the vein is desired, the catheter tube 24 must be coupled to an intravenous infusion system.

Figure 7:
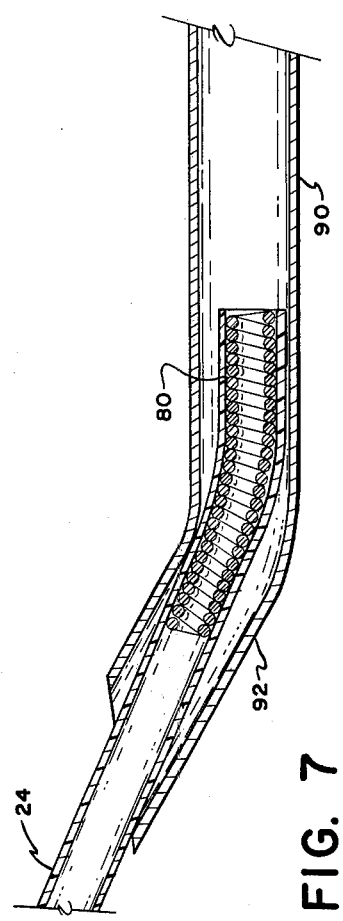
FIG. 7 is a longitudinal cross sectional view of a Tuohy caudal needle through which the catheter tube is being curvilinearly passed.
Figure 4:
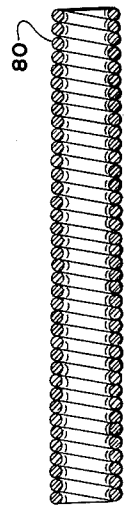
FIG. 4 is an elevational view of a hollow helical wire stiffener adapted to be placed within the hollow of the plastic cannula at the trailing end thereof.

To this end, a length of tightly wound helical spring or wire 80 is force fit into the trailing end 50 of the catheter tube so as to firmly retain the spring 80 therein without appreciably enlarging the outside diameter of the end 50. In this fashion the trailing end 50 is flexibly reinforced and an extremely effective backing is provided for reliably receiving a female adapter as hereinafter more fully explained. Furthermore, the laterally flexible nature of the trailing end 50 with the spring 80 therein effectively accommodates facile curvilinear displacement thereof through and entirely out of a curved needle, such as the Touhy caudal needle 90 having 92 near its distal tip shown in FIG. 7.

In the indicated fashion the trailing end 50 of the catheter tube 24 is thus flexibly stiffened and its outside diameter will remain essentially unchanged.

With the trailing end 50 of the catheter tube flexibly stiffened by spring sleeve 80, a female adapter of rigid plastic material, generally designated 52 is threaded or twisted upon said trailing end to create a female hub at the trailing end of the catheter tube 24. The female adapter 52 comprises a hollow body which defines a throughbore 54 comprising a tapered rear plug-receiving portion 72 into which a conventional plug 76 may be fitted. The purpose of plug 76 is to prevent blood loss during periods of catheter nonuse and preferably has breather capability as is conventional to avoid air embolism. The throughbore 54 also comprises a more sharply inwardly tapered conical section 60 and a forward portion 66, which comprises a plurality of serrations 68. The taper at portion 66 allows the adapter 52 to be "started" upon the trailing end 50 of the catheter tube 24. If desired, an additional collar of plastic such as TEFLON (a registered trademark), CLEAREX (a registered trademark) or polyvinyl chloride may be disposed to the rear of the catheter tube with the helical wire therein to receive the female adapter in the manner disclosed in copending U.S. patent application Ser. No. 704,715.

Figure 6:
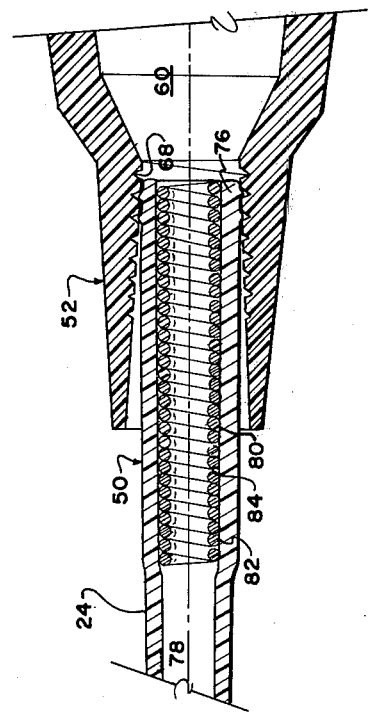
FIG. 6 is a longitudinal cross sectional view of the female adapter of FIG. 5 being twisted upon the flexibly stiffened trailing end of the catheter tube.

The nature of the serrations or threads 68 may be of any suitable type, the object being that the inside diameter of the serrations or threads or at least some portion of the serrations or threads will be less than the initial outside diameter of the trailing end 50 of the catheter tube 24 but in any event somewhat greater than the inside diameter of the catheter tube 24 at the end 50. Accordingly, as the adapter 54 and particularly the forward cylindrical projection 70 is caused to be twisted upon the trailing end 50 of the catheter tube 24 with one hand as the indwelling catheter tube is held by the other hand, the material of the end 50 is caused to be deformed into an array of exterior threads as best illustrated in FIG. 6. At the same time, interior locking threads along the interior of tube end 50 between the terms of spring 80 are caused to be made during the mentioned twisting phenomenon due to an extrusion effect. As the twisting placement of the adapter occurs it is preferred that the hand securing the catheter tube also occlude the catheter tube by applying external pressure causing its temporary collapse.

Once the threading operation has been completed, the female adapter 52 will be secured on the trailing end 50 of the plastic cannula 24 by exterior and interior serrations on tube end 50. The adapter 52 comprises conventional luer dogs or lugs 74 which facilitate fluid flow through the catheter tube 24 either from an infusion system or a syringe. The deformed plastic at end 50 creates a fluid seal and also is affixed to the adapter 52. The trailing end of the catheter tube and the adapter 52 are then taped to the arm.

It should further be appreciated that the sheath may be of transparent or translucent material so as to also define a flashback chamber.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A catheter placement assembly for displacing a catheter tube from a sterile sheath into a body cavity of a patient comprising:
   a cannulated disposable needle having a sharpened leading end;
   a substantially linear hollow semi-rigid shape-retaining disposable sheath having an axial slit therein;
   disposable hollow means connecting the trailing end of the needle to the leading end of the sheath whereby the needle, sheath and hollow means are joined together and discarded essentially simultaneously after use;
   a flexible plastic catheter tube of substantially constant diameter throughout the entire length thereof at least the trailing end of which is initially disposed within the hollow of the sheath, the trailing end of the catheter tube including laterally flexible anti-occludable hollow reinforcing means;
   catheter advancing means comprising means abutting but separable from the trailing end of the catheter tube and manually manipulatable means connected to the abutting means and laterally projecting through said slit in the sheath whereby the catheter advancing means and catheter tube are unitarily advanced and the catheter advancing means alone retracted for placement of the leading part of the catheter tube into the body cavity through the hollow of the needle following puncture, the catheter tube eventually becoming completely separated from the sheath and needle and the remainder of the assembly excluding the catheter tube being essentially unitarily discarded after said complete separation and while retaining the catheter tube within the body cavity.

2. A catheter placement assembly according to claim 1 further comprising a separate female adapter for connection to an infusion system, the separate female adapter comprising means for firmly affixing the adapter to the flexibly reinforced trailing end of the catheter tube following said separation of the remainder of the assembly from the catheter tube.

3. A catheter placement assembly for displacing a catheter tube from a sterile sheath into a body cavity of a patient comprising:
   a cannulated needle having a sharpened leading end;
   a hollow shape-retaining sheath having an axial slit therein;
   hollow means connecting the trailing end of the needle to the leading end of the sheath;
   a flexible plastic catheter tube of substantially constant diameter throughout the entire length thereof at least the trailing end of which comprises unflared anti-occludable flexible means and is initially disposed in the hollow of the sheath;
   catheter advancing means comprising means abutting substantially the entire trailing end of the catheter tube within the sheath, stylet means having a lateral dimension less than the abutting means and being connected to the abutting means and telescopically projecting a predetermined distance into the hollow of the catheter tube at the trailing end of the catheter tube and manually manipulatable reciprocable means connected to the abutting means within the sheath and comprising tab means eccentrically projecting through said slit and being exposed outside the sheath to be gripped between the fingers of the user and axially advanced and retracted along said slit whereby the catheter advancing means and the catheter may be unitarily advanced and the catheter advancing means alone retracted along the slit for placement of the leading part of the catheter tube in the body cavity through the needle following puncture, the catheter tube eventually becoming completely separated from the sheath and needle and of the remainder of the assembly excluding the catheter tube being essentially unitarily discarded while retaining the catheter tube within the body cavity.

4. A catheter placement assembly for displacing a catheter tube from a sterile sheath into the vein of a patient comprising:
   a cannulated needle having a sharpened leading end;
   a hollow semi-rigid sheath having an axial slit therein;
   hollow means connecting the trailing end of the needle to the leading end of the sheath;
   an unattached flexible catheter tube of substantially contant diameter comprising a material having the characteristic of silicone rubber, the trailing end of the catheter tube comprising flexible reinforcing means and being disposed within the hollow of the sheath with the leading end within the hollow of the needle.
   catheter advancement means comprising means abutting the trailing end of the catheter tube, stylet means connected to the abutting means and telescopically projecting a predetermined distance into the catheter tube, and manually manipulatable means connecting to the abutment means within the sheath and laterally projecting through said slit in the sheath to be gripped between the fingers of the user whereby the catheter advancing means and the catheter tube may be unitarily advanced and the catheter advancing means alone retracted for placement of the catheter tube into the vein through the needle following venipuncture and accommodate complete separation of the remainder of the assembly from the catheter tube while retaining the catheter tube within the vein; and a separate female adapter to be firmly affixed to the flexibly reinforced trailing end of the catheter tube following said separation of the remainder of the assembly from the catheter tube.

5. The catheter placement assembly of claim 4 wherein the trailing end of the catheter tube is interiorly reinforced by a coiled spring and said separate female adapter comprises a body, passageway means through the body, means at the trailing end of the body for connection to a syringe or an infusion system, and a hollow projection at the forward end of the body, the hollow of the forward projection comprising threads the inside diameter of at least some of said threads being slightly less than the outside diameter of the trailing end of the catheter tube whereby the female adapter is firmly attached to the trailing end of the catheter tube by turning it upon the catheter tube to thereby create exterior threads in the catheter tube and material at the trailing end thereof intermediate the threads within the hollow of the forward projection and also create interior threads between the turns of the spring.

6. A catheter placement assembly for displacing a catheter tube from a sterile sheath into the vein of a patient comprising:

a cannulated needle having a sharpened leading end;
a hollow semi-rigid sheath having an axial slit therein;
hollow means connecting the trailing end of the needle to the leading end of the sheath;
an unattached flexible catheter tube of substantially constant diameter comprising material having the characteristics of silicone rubber, the trailing end of the catheter tube comprising flexible reinforcing means and being disposed within the hollow of the sheath with the leading end within the hollow of the needle;
catheter advancement means comprising means abutting the trailing end of the catheter tube, stylet means connected to the abutting means and telescopically projecting a predetermined distance into the catheter tube, and manually manipulatable means connecting to the abutment means within the sheath and laterally projecting through said slit in the sheath to be gripped between the fingers of the user whereby the catheter advancing means and the catheter tube may be unitarily advanced and the catheter advancing means alone retracted for placement of the catheter tube into the vein through the needle following venipuncture and accommodate complete separation of the remainder of the assembly from the catheter tube while retaining the catheter tube within the vein;
a separate female adapter to be firmly affixed to the flexibly reinforced trailing end of the catheter tube following said separation of the remainder of the assembly from the catheter tube; and
a sterile, destructable package in which the entire catheter placement assembly is initially disposed in sealed, sterile relation.

7. A catheter comprising:
an elongated catheter tube the leading part of which is to be placed and left indwelling within the vein of a patient, the catheter tube having a substantially constant outside diameter throughout the entire length thereof; and
hollow anti-occludable means on said catheter tube and means flexibly reinforcing the interior of the trailing end of the catheter tube, said reinforcing means defining a laterally yieldable substantially constant inside surface means at the interior of said trailing end for accommodating subsequent reception of a female adapter, said hollow means further having an outside surface no larger than said outside diameter of said catheter tube.

8. A catheter comprising:
a highly pliant elongated catheter tube the leading part of which is to be placed and left indwelling within the vein of a patient, the tube comprising radiopaque silicone rubber, the catheter tube having a substantially constant outside diameter throughout the entire length thereof;
hollow anti-occludable means on said catheter tube and flexibly reinforcing the interior of the trailing end of the tube, said flexible reinforcing means defining a laterally yieldable substantially constant inside surface means and said hollow anti-occludable means having an outside surface no larger than said outside diameter of said catheter tube; and
an initially separate hollow female adapter having means for manually causing the adapter to be secured directly to the flexibly reinforced trailing end of the catheter tube at least along the exterior of the catheter tube at said trailing end.

9. An intravenous catheter assembly comprising:
an elongated catheter tube of a substantially uniform diameter and a substantially uniform wall thickness throughout the entire length thereof the leading part of which is to be placed and left indwelling within the vein of a patient through the hollow of a needle;
helical spring means force fit into the trailing end of the tube;
a needle through which the entire catheter tube and helical spring means are relatively displaced after venipuncture and while the leading part of the catheter tube is indwelling within the vein;
an initially separate hollow I.V. female adapter having means by which an I.V. set is connected to the catheter tube and means caused to forcibly engage the exterior of the catheter tube radially adjacent the helical spring means only after the catheter tube and spring means have been caused to pass entirely through the needle thereby placing the catheter tube under compression between the helical spring means and the female adapter thereby reducing the wall thickness of the catheter tube contiguous with the adapter whereby the adapter is secured to the exterior of the trailing end of the catheter tube.

10. A catheter assembly according to claim 9 wherein said needle has a curvilinear configuration.

* * * * *